US008345823B2

(12) United States Patent
Zaiki

(10) Patent No.: US 8,345,823 B2
(45) Date of Patent: Jan. 1, 2013

(54) X-RAY IMAGE DIAGNOSING APPARATUS, AND CONTROLLING METHOD OF X-RAY IMAGE DIAGNOSING APPARATUS

(75) Inventor: Ryuji Zaiki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/688,290

(22) Filed: Jan. 15, 2010

(65) Prior Publication Data
US 2010/0183116 A1   Jul. 22, 2010

(30) Foreign Application Priority Data
Jan. 19, 2009   (JP) ................................ 2009-009042

(51) Int. Cl.
*H05G 1/10* (2006.01)
(52) U.S. Cl. ............................................ 378/95; 378/62
(58) Field of Classification Search ............... 378/98.12, 378/98, 95, 62
See application file for complete search history.

(56) References Cited

U.S. PATENT DOCUMENTS
2004/0127789 A1*  7/2004  Ogawa .......................... 600/425

FOREIGN PATENT DOCUMENTS
| JP | 6-209926 | 8/1994 |
| JP | 9-75331 | 3/1997 |
| JP | 2004-236910 | 8/2004 |

* cited by examiner

*Primary Examiner* — Hoon Song
(74) *Attorney, Agent, or Firm* — Oblon, Spivak, McClelland, Maier & Neustadt, L.L.P.

(57) ABSTRACT

An X-ray image diagnosing apparatus has a radiating unit, a placement unit, a detecting unit, a supporting unit, a moving control unit, an obtaining unit, a calculating unit, and a frame rate control unit. The placement unit is placeable an object. The supporting unit supports the radiating unit and the detecting unit in opposing relationship across the placement unit. The moving control unit relatively moves the supporting unit and the object on a longwise direction of the placement unit so as to perform an X-ray imaging at different imaging positions along the longwise direction. The obtaining unit obtains X-ray image by performing the X-ray imaging. The calculating unit calculates blood-vessel data on the basis of the X-ray image and calculates a frame rate on the basis of the blood-vessel data. The frame rate control unit configured to change the frame rate on the X-ray imaging.

20 Claims, 11 Drawing Sheets

X-RAY IMAGE DIAGNOSING APPARATUS, AND CONTROLLING METHOD OF X-RAY IMAGE DIAGNOSING APPARATUS

BACKGROUND OF THE INVENTION

1. Field of the Invention

The present invention relates to an X-ray image diagnosing apparatus and a controlling method of that for displaying a plurality of X-ray images acquired in different positions.

2. Description of the Related Art

A known X-ray image diagnosing apparatus for acquiring an image of blood vessels in which contrast is enhanced using a contrast medium includes an X-ray source and an FPD or an I. I. equipped at both ends of a substantially C-shaped holder (C-arm), respectively, and an image processing unit. This X-ray image diagnosing apparatus is generally also referred to as an angiography apparatus, which allows diagnosis and treatment (medical treatment), such as insertion of a catheter into an object such as a patient by a doctor, and acquisition of an X-ray image.

One of examinations using the X-ray image diagnosing apparatus is a lower-extremity angiography examination. In the lower-extremity angiography examination, an image of the entire long and narrow image-acquisition region from the abdomen to the tiptoe is acquired while a contrast medium injected through a catheter proceeded to the abdominal aorta is traced. In the acquisition of an image of the entire image-acquisition region, the entire image cannot be acquired at a time, so that images of the entire image-acquisition region are acquired in several times. In this case, injecting the contrast medium every image-acquisition exerts a large burden on the patient. Therefore, a method for acquiring an image of the entire image-acquisition region from the abdomen to the tiptoe by one injection of the contrast medium was devised. When a proper quantity of contrast medium is injected, the part dyed with the contrast medium flows from the abdomen toward the tiptoe in the blood stream. The image-acquisition is repeated while the stream is traced.

There are two kinds of image-acquisition method, that is, bolus-chase angiography and stepping angiography. The mask images of the entire image-acquisition region are collected using either of the two kinds of image-acquisition method, and after a contrast medium is injected into the patient, the contrast images of the entire image-acquisition region are collected to execute a digital subtraction angiography (DSA). Then, the mask images and the contrast images are subjected to subtraction processing in which they are differentiated every image-acquisition position to generate difference images (DSA images). When the plurality of DSA images at the image-acquisition positions are bonded together, a long image that displays the entire image-acquisition region from the abdomen to the lower extremity in which all the blood vessels are drawn is generated.

As an art related to the present invention, Japanese Unexamined Patent Application Publication No. 2004-236910 is disclosed.

However, with this related art, if X-ray exposure is performed at a fixed frame rate, DSA images taken at a plurality of image-acquisition positions each include a portion that can be sufficiently checked (diagnosed) with one DSA image, which will increase the amount of X-ray exposure of the patient.

Moreover, in angiography of narrow blood vessels, such as those of a lower extremity, the narrow blood vessels are lost in the noise on the DSA images, thus sometimes making it difficult to view the running blood vessels.

Furthermore, it is necessary for the DSA to set (register) image-acquisition positions in advance, which is inefficient for the operator to execute X-ray diagnosis.

SUMMARY OF THE INVENTION

The present invention is made in consideration of the above-described circumstances. Accordingly, it is an object of the present invention to provide an X-ray image diagnosing apparatus and a controlling method of that in which X-ray exposure of a patient can be reduced and an optimum X-ray image diagnosing environment for the operator can be provided.

To solve the above-described problems, the present invention provides the X-ray image diagnosing apparatus comprising: a radiating unit configured to radiate X-rays; a placement unit which is placeable an object; a detecting unit configured to detect X-rays that passed through the object; a supporting unit configured to support the radiating unit and the detecting unit in opposing relationship across the placement unit; a moving control unit configured to relatively move the supporting unit and the object on a longwise direction of the placement unit so as to perform an X-ray imaging at different imaging positions along the longwise direction; an obtaining unit configured to obtain X-ray image by performing the X-ray imaging; a calculating unit configured to calculate blood-vessel data indicating at least one of diameters and concentrations of blood vessels on the basis of the X-ray image, and to calculate a frame rate on the basis of the blood-vessel data; and a frame rate control unit configured to change the frame rate on the X-ray imaging.

To solve the above-described problems, the present invention provides the X-ray image diagnosing apparatus comprising: a radiating unit configured to radiate X-rays; a placement unit which is placeable an object; a detecting unit configured to detect X-rays that passed through the object; a supporting unit configured to support the radiating unit and the detecting unit in opposing relationship across the placement unit; a moving control unit configured to relatively move the supporting unit and the object on a longwise direction of the placement unit so as to perform an X-ray imaging at different imaging positions along the longwise direction; a setting unit configured to preliminarily set an imaging condition that respective frame rates and the respective imaging positions are associated with each other; and an obtaining unit configured to obtain X-ray image by performing the X-ray imaging on the frame rates corresponding to the respective imaging positions in accordance with the imaging condition.

To solve the above-described problems, the present invention provides the controlling method of the X-ray image diagnosing apparatus including a radiating unit configured to radiate X-rays, a placement unit which is placeable an object, a detecting unit configured to detect X-rays that passed through the object, and a supporting unit configured to support the radiating unit and the detecting unit in opposing relationship across the placement unit, comprising: a moving control step of relatively moving the supporting unit and the object on a longwise direction of the placement unit so as to perform an X-ray imaging at different imaging positions along the longwise direction; an obtaining step of obtaining X-ray image by performing the X-ray imaging; a calculating step of calculating blood-vessel data indicating at least one of diameters and concentrations of blood vessels on the basis of the X-ray image, and calculating a frame rate on the basis of the blood-vessel data; and a frame rate control step of changing the frame rate on the X-ray imaging.

To solve the above-described problems, the present invention provides the controlling method of the X-ray image diagnosing apparatus including a radiating unit configured to radiate X-rays, a placement unit which is placeable an object, a detecting unit configured to detect X-rays that passed through the object, and a supporting unit configured to support the radiating unit and the detecting unit in opposing relationship across the placement unit, comprising: a moving control step of relatively moving the supporting unit and the object on a longwise direction of the placement unit so as to perform an X-ray imaging at different imaging positions along the longwise direction; a setting step of preliminarily setting an imaging condition that respective frame rates and the respective imaging positions are associated with each other; and an obtaining step of obtaining X-ray image by performing the X-ray imaging on the frame rates corresponding to the respective imaging positions in accordance with the imaging condition.

DESCRIPTION OF THE PREFERRED EMBODIMENTS

X-ray image diagnosing apparatuses and controlling methods of those according to embodiments of the present invention will be described with reference to the attached drawings.

An angiography apparatus, or an X-ray image diagnosing apparatus, includes a digital subtraction angiography (DSA) mode. In the DSA imaging mode, X-ray transmission images (mask images) that do not include an image of a contrast medium and 2-D X-ray transmission images (contrast images or live images) that include an image of a contrast medium are subjected to subtraction processing to generate difference images (DSA images), and the DSA images can be displayed or stored.

Figure 1:
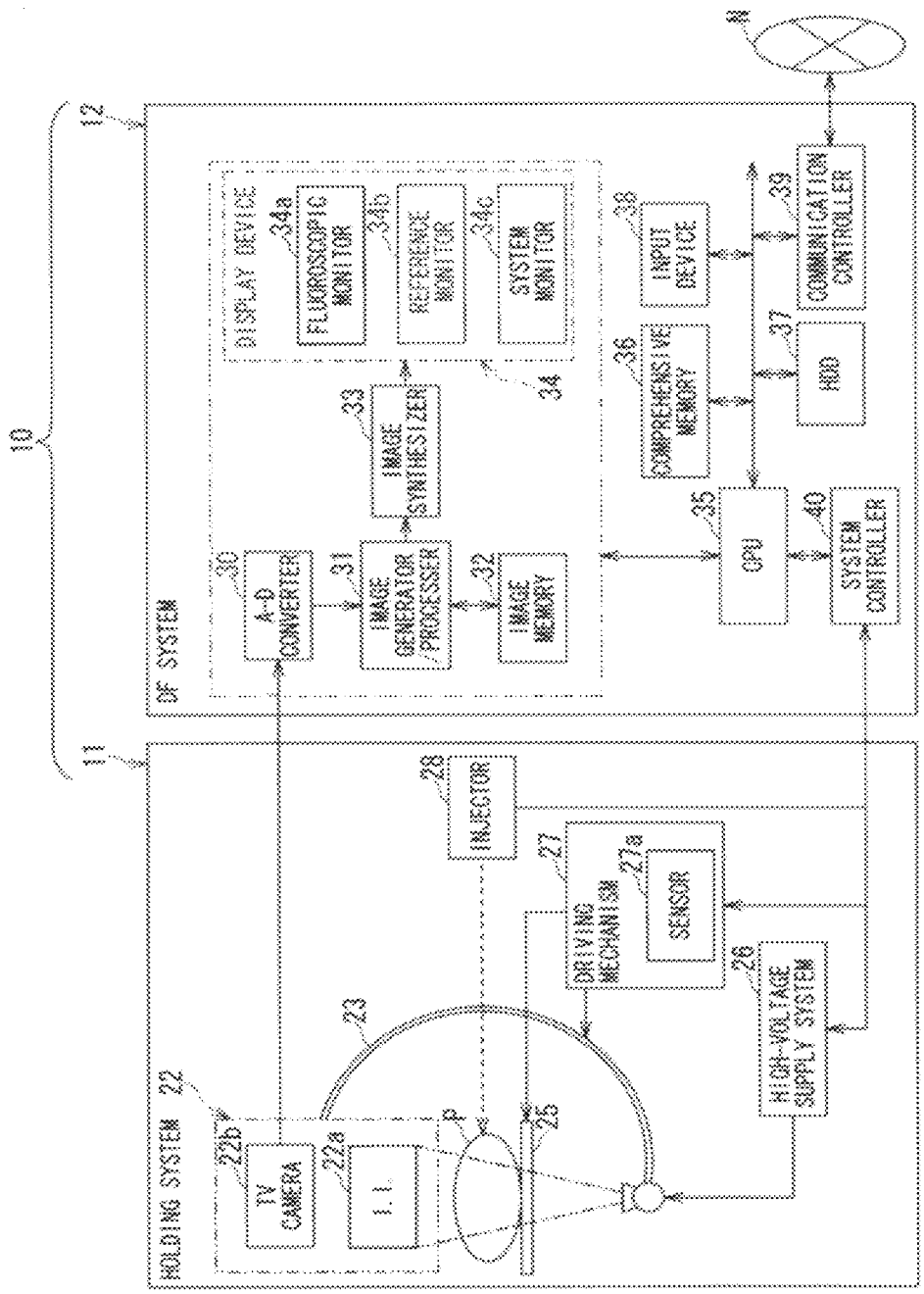
FIG. 1 is a schematic diagram showing an example of the hardware configuration of an X-ray image diagnosing apparatus of present embodiments.

FIG. 1 is a schematic diagram showing an example of the hardware configuration of an X-ray image diagnosing apparatus of a first embodiment.

Referring to FIG. 1, the angiography apparatus 10, or the X-ray image diagnosing apparatus, is broadly constituted of a holding system 11 and a DF system 12.

The holding system 11 includes an X-ray source (tube) 21, a X-ray detector 22, a C-arm 23, a table-top (catheter table) 25, a high-voltage supply system 26, a driving mechanism 27, and an automatic contrast-medium injecting system (injector) 28. Note that the holding system 11 in this case is of an under tube type in which the X-ray source 21 is located below the table-top 25; alternatively, the X-ray source 21 may be of an over tube type in which the X-ray source 21 is located above the table-top 25. Furthermore, an X-ray radiation field aperture diaphragm composed of a plurality of lead blades and a compensating filter formed of silicon rubber or the like for attenuating a predetermined amount of X-rays may be equipped to prevent halation.

The X-ray source 21 is equipped at one end of the C-arm 23 and emits X-rays toward an object (patient) P on the table-top 25 depending on the condition of high-voltage electric power supplied from the high-voltage supply system 26.

The X-ray detector 22 is equipped at the other end of the C-arm 23 and at the exiting side of the X-ray source 21 and detects X-rays passed through the patient P on the table-top 25. The X-ray detector 22 is based on an image intensifier (I. I.)—TV system, and has an I. I. 22a and a TV camera 22b.

The I. I. 22a converts X-rays that passed through the patient P to visible light and doubles the luminance in the course of light—electrons—light conversion to form highly sensitive projection data. The TV camera 22b converts the optical projection data to an electric signal using a charge coupled device (CCD) image sensor.

The C-arm 23 supports the X-ray source 21 at one end thereof and the X-ray detector 22 at the other end in opposing relationship about the patient P. The amount, timing, and speed of the movement of the C-arm 23 are controlled by the driving mechanism 27.

The table-top 25 is used to place the patient P thereon. The high-voltage supply system 26 supplies high-voltage electric power to the X-ray source 21 under the control of the DF system 12.

The driving mechanism 27 moves the C-arm 23 in a circular direction of the C-arm 23 (a left anterior oblique view (LAO) direction, or a right anterior oblique view (CRA) direction), and a swinging direction (a cranial view (CRA), or a caudal view (CAU) direction).

When performing a lower-extremity angiography examination using the angiography apparatus 10, the operator takes images of the entire long and narrow image-acquisition region from the abdomen to the tiptoe in a plurality of times while tracing a contrast medium injected through a catheter proceeded to the abdominal aorta of the patient P on the table-top 25, because the entire image-acquisition region is longer than the width of the I. I. 22a (the length of the table-top 25 in the longitudinal direction). Thus, the driving mechanism 27 can change the relative positions of the C-arm 23 and the table-top 25 in the longitudinal direction during image-acquisition in accordance with the control of the DF system 12. For example, the driving mechanism 27 moves the C-arm 23 parallel to the table-top 25 along the length of the table-top 25 in accordance with the control of the DF system 12. Alternatively, the driving mechanism 27 moves the table-top 25 parallel to the C-arm 23 along the length of the table-top 25 in accordance with the control of the DF system 12. In this embodiment, the former one is adopted.

Furthermore, the driving mechanism 27 moves the C-arm 23 and the table-top 25 up and down together in accordance with the control of the DF system 12. In addition, the driving mechanism 27 moves the table-top 25 vertically, horizontally, and longitudinally in accordance with the control of the DF system 12. The driving mechanism 27 includes a sensor 27a for measuring the moving distance of the table-top 25 when translating the table-top 25 in the longitudinal direction.

The injector 28 is a unit for injecting a contrast medium into a catheter (catheter tube (not shown)) inserted into the abdominal aorta of the patient P under the control of the DF system 12.

On the other hand, the DF system 12 is based on a computer, so that it can mutually communicate with a main network N, such as a local area network (LAN), of the hospital. The DF system 12 is broadly constituted of hardware, such as an analog to digital (A-D) converter 30, an image generator/processor 31, an image memory 32, an image synthesizer 33, a display device 34, a central processing unit (CPU) 35 serving as a processor, a comprehensive memory 36, a hard disc drive (HDD) 37, an input device 38, a communication controller 39, and a system controller 40. The CPU 35 is mutually connected to the individual hardware components that constitute the DF system 12 via a bus serving as a common signal transmission line. The DF system 12 may include a drive (not shown) for a recording medium.

The A-D converter 30 converts a time-series analog signal (video signal) output from the X-ray detector 22 to a digital signal.

The image generator/processor 31 performs a logarithmic conversion process (LOG process) on the digital signal of the projection data output from the A-D converter 30, performs an adding operation as necessary to generate image data (a mask images and a contrast images) for each frame, and stores the image data in the image memory 32 under the control of the CPU 35. The image generator/processor 31 performs image processing on the image data per frame and stores the processed image data in the image memory 32. Examples of the image processing include image-data magnification/gradation/spatial filtering processes, a minimum value/maximum value tracing process on image data that is accumulated in time series, a subtraction process, and an adding operation for removing noise. Image data, such as difference images (DSA images), subjected to the subtraction process by the image generator/processor 31 is output to the image synthesizer 33 and is stored in a storage unit, such as the image memory 32.

The image memory 32 stores image data output from the image generator/processor 31 under the control of the CPU 35. The DSA images to be stored in the image memory 32 are given patient information, image-acquisition position information (table position and stage), image-acquisition-time information, etc.

The image synthesizer 33 combines the image data output from the image generator/processor 31 with character information, a scale, etc. of various parameters and outputs it as a video signal to the display device 34 under the control of the CPU 35. Specifically, the image synthesizer 33 combines the DSA images from the image generator/processor 31 with character information, a scale, etc. of various parameters and outputs it as a video signal to the display device 34.

Figure 2:
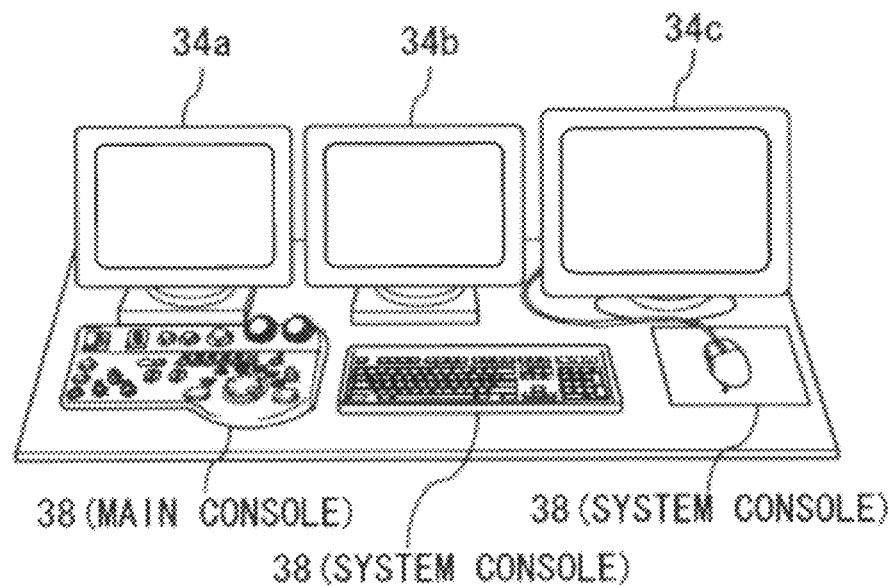
FIG. 2 is a diagram showing an example of an arrangement of a display device that constitutes the X-ray image diagnosing apparatus of present embodiments.

FIG. 2 is a diagram showing an example of the arrangement of the display device 34 that constitutes the angiography apparatus 10.

The display device 34 includes a fluoroscopic monitor 34a, a reference monitor 34b, and a system monitor 34c. The fluoroscopic monitor 34a, the reference monitor 34b, and the system monitor 34c are each constituted of a liquid crystal display, a cathode ray tube (CRT), or the like.

The display device 34 shown in FIG. 1 further includes a display image memory, such as a video random access memory (VRAM, not shown), a digital to analog (D-A) converter (not shown), and a display circuit. Image data to be displayed is displayed on the display device 34 in such manner that the image data is developed in the VRAM under the control of the CPU 35.

The fluoroscopic monitor 34a displays a mask image, a contrast image, etc. output from the image synthesizer 33 as live images.

The reference monitor 34b displays the DSA image output from the image synthesizer 33 as a still image or displays DSA images as reproduced moving images.

The system monitor 34c mainly displays data for controlling the holding system 11, such as data for switching a field of view (FOV).

The CPU 35 is a control unit having a large scale integration (LSI) configuration in which a semiconductor electronic circuit is sealed in a package having a plurality of terminals. When an instruction is input through an operation on the input device 38 by an operator, such as a doctor or a radiographer, the CPU 35 executes a program stored in the comprehensive memory 36. Alternatively, the CPU 35 loads, in the comprehensive memory 36, a program that is stored in the HDD 37, a program transferred via the network N, received by the communication controller 39, and installed in the HDD 37, or a program that is read from a recording medium mounted in the recording-medium drive (not shown) and installed in the HDD 37 and executes the program.

The comprehensive memory 36 is a storage unit having storage elements, such as both a read only memory (ROM) and a random access memory (RAM). The comprehensive memory 36 is a storage unit that is used for an initial program loading (IPL), a basic input/output system (BIOS), storage of data, or temporary storage of the work memory of the CPU 35 and data.

The HDD 37 is a storage unit having a configuration in which a metal disk to which a magnetic substance is applied or evaporated is undetachably built. The HDD 37 stores programs (including application programs installed in the DF system 12 and also an operating system (OS)) and data. The OS may also be provided with a graphical user interface (GUI) that uses many graphics to display information for the user so that the user can perform basic operations with the input device 38.

The input device 38 includes a keyboard, a mouse, or the like that is operable by the operator, through which an input signal according to an operation is transmitted to the CPU 35. The input device 38 is broadly constituted of a main console or a system console.

The communication controller 39 performs communication control according to individual specifications. The communication controller 39 has a function capable of connecting to the network N. Thus, the angiography apparatus 10 can connect to the network N via the communication controller 39.

The system controller 40 includes a CPU and a memory (not shown). The system controller 40 controls the operations of the high-voltage supply system 26, the driving mechanism 27, the injector 28, etc. of the holding system 11 in accordance with an instruction from the CPU 35.

Figure 3:
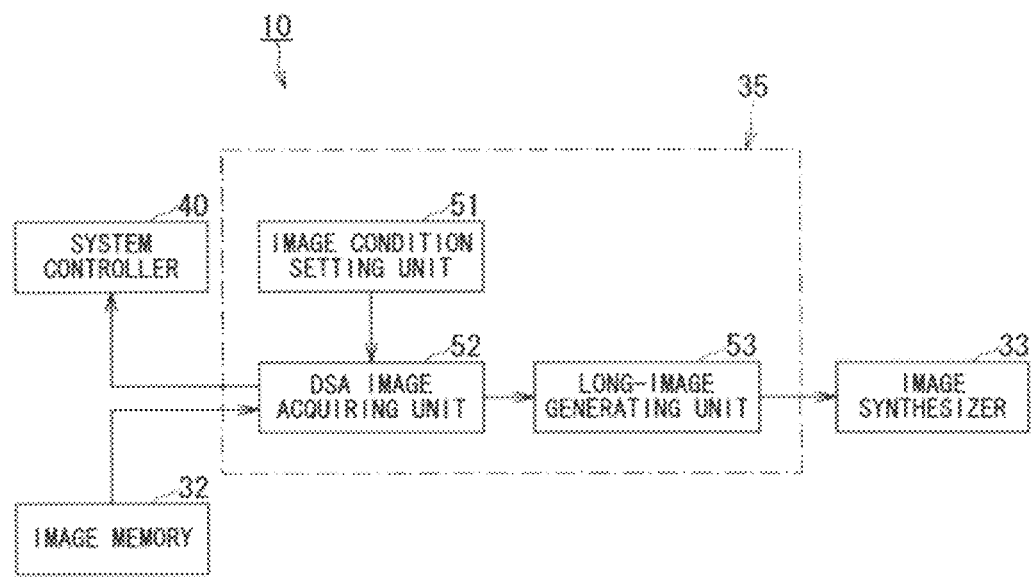
FIG. 3 is a block diagram showing functions of the X-ray image diagnosing apparatus of a first embodiment.

FIG. 3 is a block diagram showing the functions of the angiography apparatus 10 of the first embodiment.

When the CPU 35 of the DF system 12 in the angiography apparatus 10 shown in FIG. 1 executes programs, the angiography apparatus 10 functions as an image condition setting unit 51, a DSA image acquiring unit 52, and a long-image generating unit 53. Although the components 51 to 53 are described as the functions of the CPU 35, the present invention is not limited thereto; the components 51 to 53 may be provided as hardware in the DF system 12.

The image condition setting unit 51 has the function of setting an image condition including a plurality of different frame rates (image-acquisition intervals) in advance in executing DSA imaging by moving the table-top 25 (patient P) along the length of the table-top 25 with respect to the C-arm 23. For example, the image condition setting unit 51 sets the image condition including the frame rates so that the frame rates from the abdomen (upper body) to the tiptoe (lower body) of the entire image-acquisition region including the lower extremity gradually increase.

The DSA image acquiring unit 52 has the function of controlling the system controller 40 in accordance with the image condition set by the image condition setting unit 51 to execute the DSA imaging of the entire image-acquisition region and the function of acquiring DSA images, or contrast images, at a plurality of image-acquisition positions from the image memory 32. The DSA image acquiring unit 52 performs the DSA imaging for collecting mask images of the entire image-acquisition region by stepping angiography, and after a contrast medium is injected into the patient P, collecting contrast images of the entire image-acquisition region by stepping angiography. The DSA image acquiring unit 52 then performs a subtraction process whereby the mask images and the contrast images are differentiated for the individual image-acquisition positions to generate difference images (DSA images). The DSA images generated by the DSA image acquiring unit 52 are stored in a storage unit, such as the image memory 32, together with the positional information of the table-top 25 acquired from the sensor 27a, image-acquisition-time information, etc.

In the stepping angiography, the table-top 25 is moved to an image-acquisition position earlier than the arrival of the contrast medium in accordance with a first frame rate of the frame rates included in the image condition that is set by the image condition setting unit 51 and is stopped there, and an image is acquired, with the table-top 25 stopped. After the image-acquisition at the image-acquisition position is completed, the table-top 25 is moved and stopped in accordance with a second frame rate of the frame rates included in the image condition, and an image is acquired, with the table-top 25 stopped again. That is, the stepping angiography is a method for image-acquisition in which the table-top 25 is intermittently move in accordance with various frame rates to cover the entire image-acquisition region with the intermittent movement of the table-top 25. In the stepping angiography, the DSA image acquiring unit 52 controls the system controller 40 in accordance with various frame rates to give an instruction to repeat the movement and stop of the table-top 25 and image-acquisition.

The long-image generating unit 53 has the function of generating a long image indicating the entire image of the lower extremity on the basis of the DSA images acquired by the long-image generating unit 53. The long image generated by the long-image generating unit 53 is displayed (longitudinally displayed) on the reference monitor 34b of the display device 34 via the image synthesizer 33.

For example, the long-image generating unit 53 executes a partially overlapping process in accordance with stage information on the basis of DSA images acquired in different positions by the long-image generating unit 53 to generate a long image indicating the entire low extremity. For example, the long-image generating unit 53 extracts the edges of blood vessels on the basis of a difference in luminance on the DSA images and executes the partially overlapping process to connect the blood vessels to generate a long image indicating the entire low extremity.

Note that a signal to noise (S/N) ratio can be improved when the long-image generating unit 53 takes the luminance value of a portion at which DSA images coincide as the average value of luminance values corresponding to the portion, determines that luminance values lower than a certain level is noise, and filters them. Since there may be branches of the blood vessels in the vicinity of the edges thereof, the long-image generating unit 53 performs the filtering not by comparing the average value with a fixed noise detecting threshold value (gain) but by comparing the average value with a weighted noise detecting threshold value.

Figure 4:
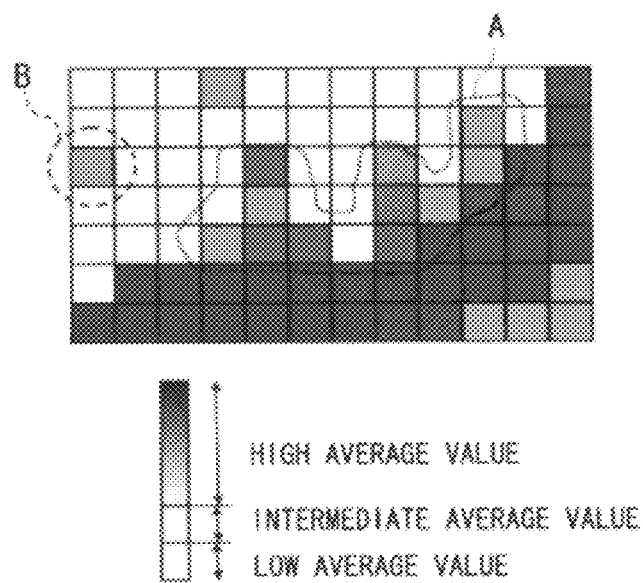
FIG. 4 is a diagram showing average values at individual pixels in vicinity of branches of blood vessels.
Figure 5:
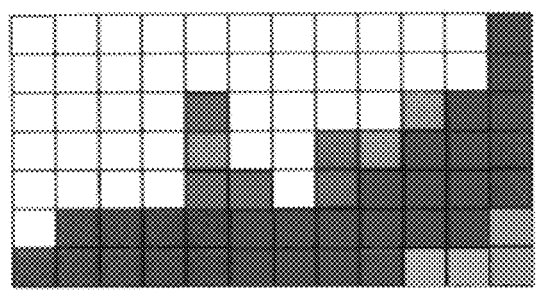
FIG. 5 is a diagram showing luminance values at the individual pixels in the vicinity of the branches of the blood vessels after filtering.

FIG. 4 is a diagram showing the average values at individual pixels in the vicinity of the branches of blood vessels. FIG. 5 is a diagram showing luminance values at the individual pixels in the vicinity of the branches of the blood vessels after filtering.

As shown in FIG. 4, the average values of the individual pixels are classified into a high average value (apparent blood vessel images), an intermediate average value (unclear whether it is a blood vessel image or noise), and a low average value (apparent noise). Pixels corresponding to the intermediate average value are determined whether they are the edges of blood vessels from the average values of surrounding pixels (the noise detecting threshold value is changed). For example, pixels in region A with the intermediate average value, in which surrounding pixels have a fixed luminance level or higher, are subjected to filtering using a larger noise detecting threshold value in consideration of the possibility that the pixels are branches of the blood vessels. For pixels in region B whose surrounding pixels have a fixed luminance level or lower shown in FIG. 4, a smaller noise detecting threshold is used.

To improve the S/N ratio, the long-image generating unit 53 may set the luminance value of a portion at which DSA images overlap as the most numerous value of the plurality of luminance values corresponding to the portion.

Figure 6:
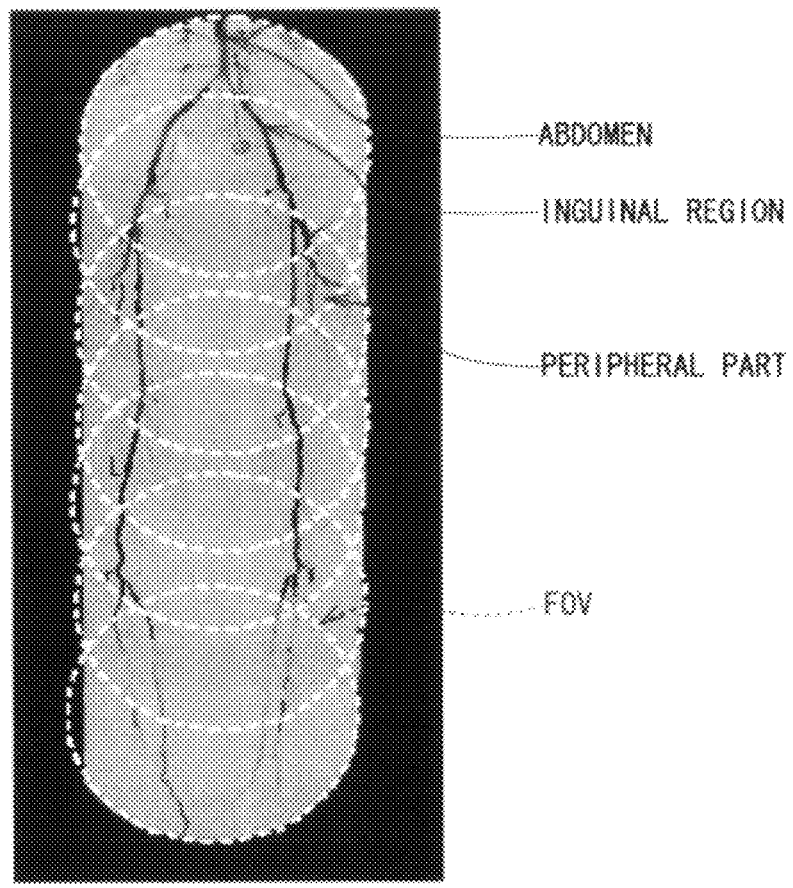
FIG. 6 is a diagram showing a relationship between a long image and individual FOVs of the long image with a known single frame rate.
Figure 7:
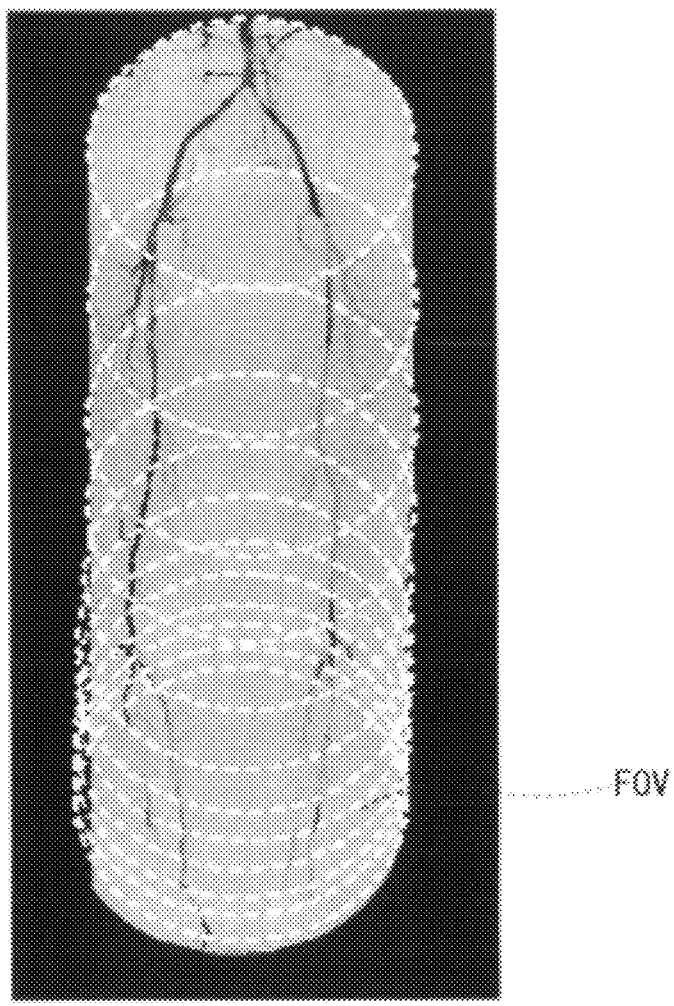
FIG. 7 is a diagram showing a relationship between a long image and the individual FOVs of the long image with the imaging by the image condition according to the first embodiment.

FIG. 6 is a diagram showing a relationship between the long image and the individual FOVs of the long image with a known single frame rate. FIG. 7 is a diagram showing a relationship between the long image and the individual FOVs of the long image with the imaging by the image condition according to the first embodiment.

As shown in FIG. 6, when the DSA imaging is performed using the known single frame rate, the region from the abdomen to the inguinal region that can be sufficiently checked (diagnosed) using one DSA image is also exposed several times, which increases an exposure amount of the patient P. Moreover, images of narrow blood vessels, such as peripheral blood vessels, are lost in noise, sometimes making it difficult to view the running blood vessels.

On the other hand, as shown in FIG. 7, when the DSA imaging is performed using the imaging condition of the first embodiment, the exposure of the patient P can be decreased by reducing the number of image-acquisitions for the region from the abdomen to the inguinal region by decreasing the frame rate because the region from the abdomen to the inguinal region has so thick blood vessels that it is easy to view. On the other hand, the number of image-acquisitions is increased for the peripheral blood vessels by increasing the frame rate because the peripheral blood vessels are sometimes lost in noise.

With the angiography apparatus 10 of the first embodiment, the number of image-acquisitions of thick blood vessels can be decreased, so that X-ray exposure of the patient P can be reduced. Moreover, with the angiography apparatus 10, image-acquisition positions are automatically set depending on the frame rates that constitute the image condition, so that there is no need for the operator to set image-acquisition positions in advance. Thus, an optimum X-ray diagnosis environment for the operator can be provided.

Figure 8:
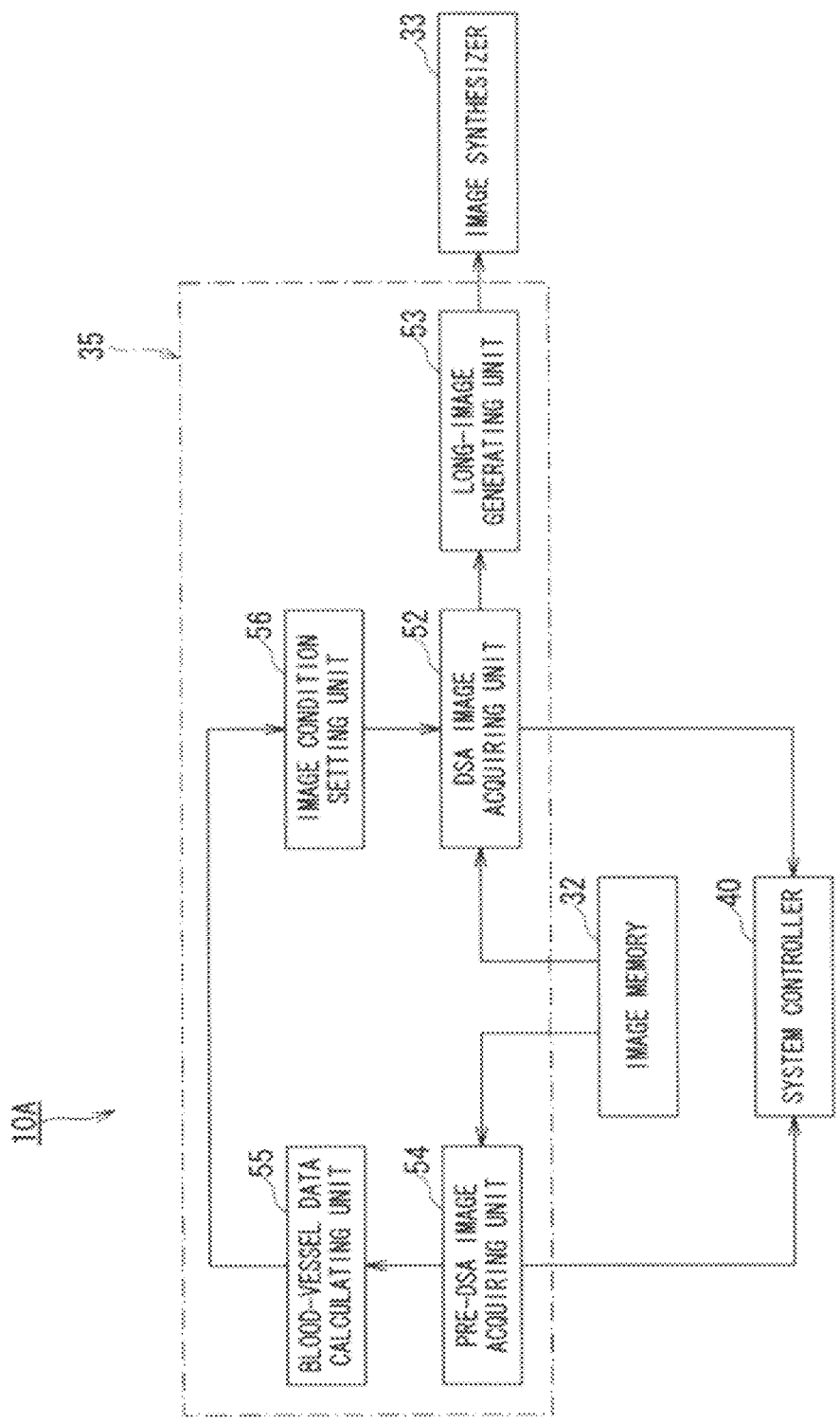
FIG. 8 is a block diagram showing functions of the X-ray image diagnosing apparatus of a second embodiment.

FIG. 8 is a block diagram showing the functions of an angiography apparatus 10A of a second embodiment. Since the hardware configuration of the angiography apparatus 10A of the second embodiment is the same as that of the angiography apparatus 10 of the first embodiment shown in FIGS. 1 and 2, a description thereof will be omitted.

When the CPU 35 shown in FIG. 1 executes programs, the angiography apparatus 10A functions as the DSA image acquiring unit 52, the long-image generating unit 53, a pre-DSA image acquiring unit 54, a blood-vessel data calculating unit 55, and an image condition setting unit 56. Although the components 52 to 56 are described as the functions of the CPU 35, the present invention is not limited thereto; the components 52 to 56 may be provided as hardware in the DF system 12. The same functions of the angiography apparatus 10A shown in FIG. 8 as those of the angiography apparatus 10 shown in FIG. 3 are given the same reference numerals, and descriptions thereof will be omitted.

Figure 9:
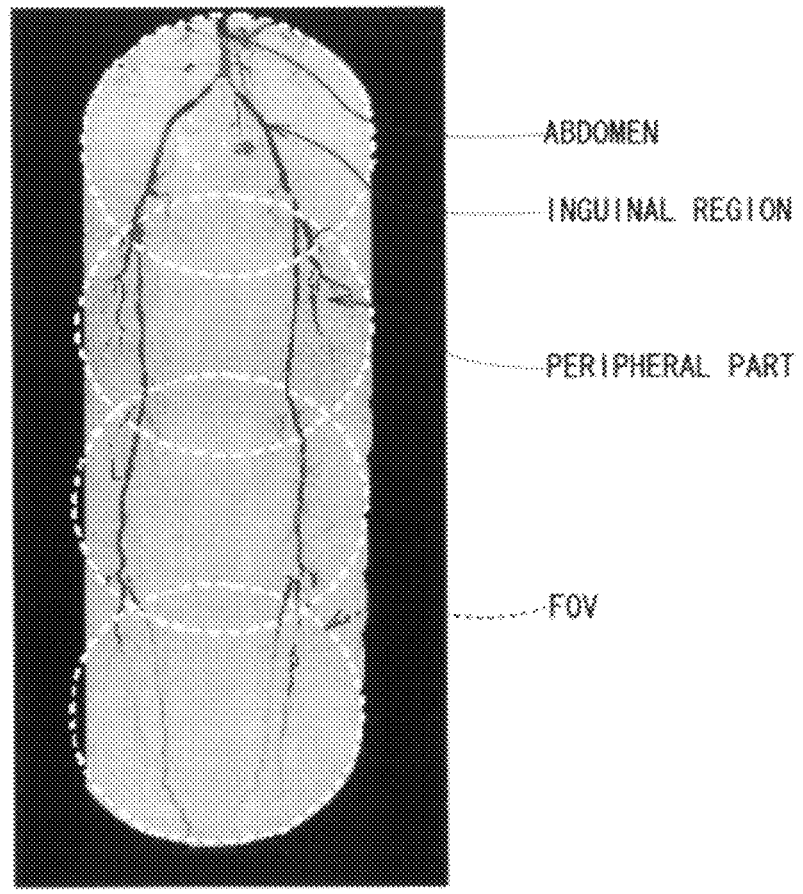
FIG. 9 a diagram showing a relationship between the long image and the FOVs of the long image by a pilot DSA angiography.

The pre-DSA image acquiring unit 54 has the function of controlling the system controller 40 in accordance with a relatively low fixed frame rate for pilot angiography to execute the DSA imaging of the entire image-acquisition region including the extremity of the patient P and the function of acquiring a plurality of DSA images (contrast images) at individual image-acquisition positions from the image memory 32. FIG. 9 shows the relationship between a long image and the FOVs of the long image by the pilot DSA angiography.

The blood-vessel data calculating unit 55 has the function of extracting blood vessels using the luminance of the pre-DSA images acquired by the pre-DSA image acquiring unit 54 and calculating at least one of the diameters of the blood vessels and the luminance values of the blood vessels (the concentration of the contrast medium) as blood-vessel data. A method for calculating the blood-vessel data will be described later with reference to FIG. 11.

The image condition setting unit 56 has the function of setting a image condition including different frame rates in advance for executing the DSA imaging while moving the table-top 25 in the longitudinal direction with respect to the C-arm 23. For example, if the blood vessel diameters calculated by the blood-vessel data calculating unit 55 are greater than or equal to a threshold value, the image condition setting unit 56 sets a low frame rate, and if the blood vessel diameters are smaller than the threshold value, the image condition setting unit 56 sets a high frame rate. The DSA image acquiring unit 52 controls the system controller 40 in accordance with the image condition set by the image condition setting unit 56 to execute the DSA imaging of the extremity of the patient P.

With the angiography apparatus 10A of the second embodiment, the number of image-acquisitions of thick blood vessels can be decreased, so that W-ray exposure of the patient P can be reduced. Moreover, with the angiography apparatus 10A, image-acquisition positions are automatically set depending on the frame rates that constitute the image condition, so that there is no need for the operator to set image-acquisition positions in advance. Thus, an optimum X-ray diagnosis environment for the operator can be provided.

Figure 10:
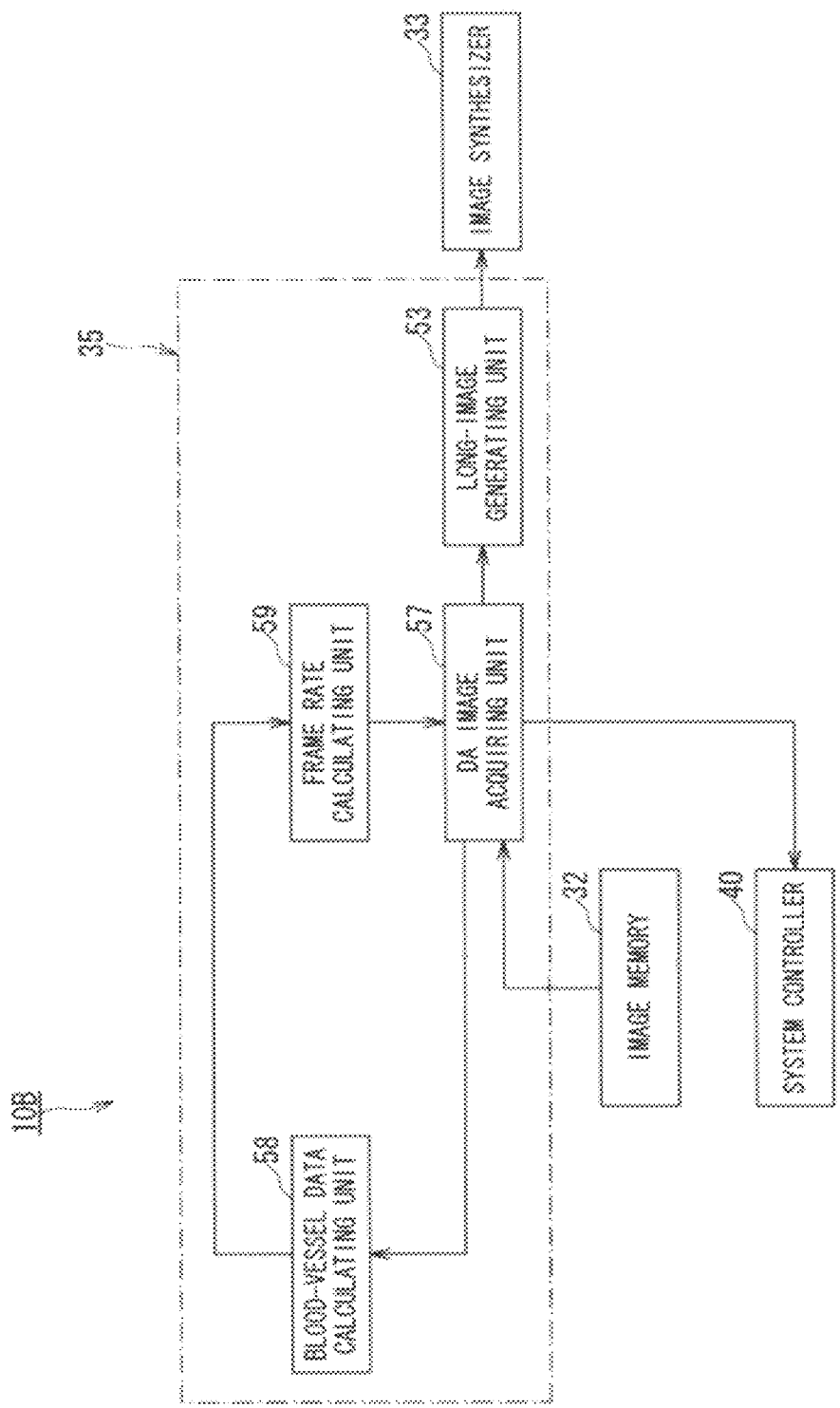
FIG. 10 is a block diagram showing functions of the X-ray image diagnosing apparatus of a third embodiment.

FIG. 10 is a block diagram showing the functions of an angiography apparatus 10B of a third embodiment. Since the hardware configuration of the angiography apparatus 10B of the third embodiment is the same as that of the angiography apparatus 10 of the first embodiment shown in FIGS. 1 and 2, a description thereof will be omitted.

When the CPU 35 shown in FIG. 1 executes programs, the angiography apparatus 10B functions as the long-image generating unit 53, a digital angiography (DA) image acquiring unit 57, a blood-vessel data calculating unit 58, and a frame rate calculating unit 59. Although the components 53 and 57 to 59 are described as the functions of the CPU 35, the present invention is not limited thereto; the components 53 and 57 to 59 may be provided as hardware in the DF apparatus 12. The functions of the angiography apparatus 10B shown in FIG. 10 are given the same reference numerals as those of the angiography apparatus 10 shown in FIG. 3, and descriptions thereof will be omitted.

The DA image acquiring unit 57 has the function of controlling the system controller 40 in accordance with a frame rate that is appropriately calculated by the frame rate calculating unit 59 to execute the DA imaging of the entire image-acquisition region and the function of acquiring DA images (contrast images) from the image memory 32. The DA image acquiring unit 57 performs DA imaging for collecting DA images of the entire image-acquisition region by stepping angiography after a contrast medium is injected into the patient P. The DA images generated by the DA image acquiring unit 57 are stored in a storage unit, such as the image memory 32, together with the positional information of the table-top 25 acquired from the sensor 27a, image-acquisition-time information, etc. The DA images acquired by the DA image acquiring unit 57 are displayed on the fluoroscopic monitor 34a substantially in real time.

The blood-vessel data calculating unit 58 has the function of extracting blood vessels using the luminance of the DA images that are appropriately acquired by the DA image acquiring unit 57 and calculating at least one of the diameters of the blood vessels and the luminance values of the blood vessels (the concentration of the contrast medium) as blood-vessel data.

Figure 11:
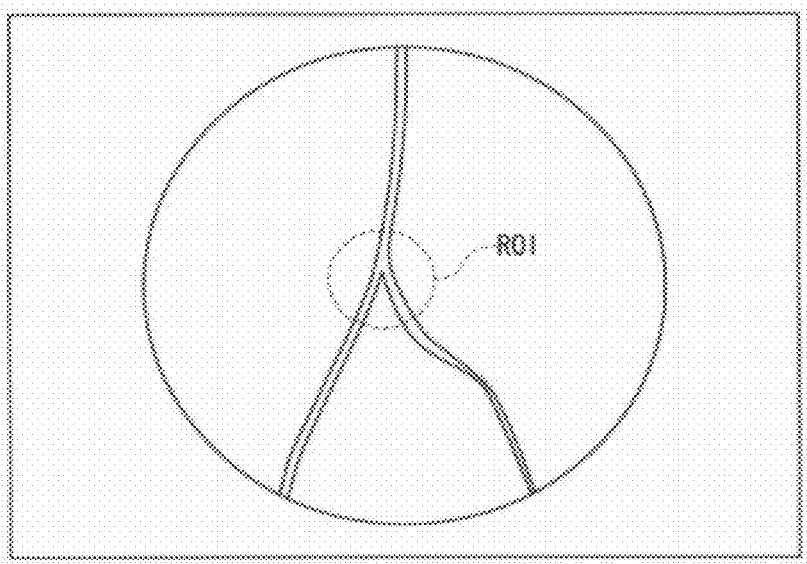
FIG. 11 is a schematic diagram for explaining a method for calculating blood-vessel data.

FIG. 11 is a schematic diagram for explaining a method for calculating the blood-vessel data.

FIG. 11 shows a blood vessel in the FOV of a DA image acquired by the DA image acquiring unit 57. As shown in FIG. 11, the blood-vessel data calculating unit 58 extracts a blood vessel in a region of interest (ROI) of the DA image acquired by the DA image acquiring unit 57 and calculates at least one of the average value of the diameters of the extracted blood vessels and the average value of the luminance values of the blood vessels as the blood-vessel data. Although not shown, the blood-vessel data calculating unit 58 extracts a blood vessel in the vicinity of the center of the DA image acquired by the DA image acquiring unit 57 and calculates at least one of the average value of the diameters of the extracted blood vessel and the average value of the luminance values of the blood vessel as the blood-vessel data.

The frame rate calculating unit 59 has the function of calculating the next frame rate on the basis of the blood-vessel data that is appropriately calculated by the blood-vessel data calculating unit 58 while moving the table-top 25 in the longitudinal direction with respect to the C-arm 23. For example, for an image-acquisition position at which the blood vessel diameter calculated by the blood-vessel data calculating unit 58 is greater than or equal to a threshold value, the frame rate calculating unit 59 sets a low frame rate, and for an image-acquisition position at which the blood vessel diameter is smaller than the threshold value, the frame rate calculating unit 59 sets a high frame rate. Alternatively, for an image-acquisition position at which the luminance value of the blood vessel calculated by the blood-vessel data calculating unit 58 is greater than or equal to a threshold value, the frame rate calculating unit 59 sets a low frame rate, and for an image-acquisition position at which the luminance value of the blood vessel is smaller than the threshold value, the frame rate calculating unit 59 sets a high frame rate. The DA image acquiring unit 57 controls the system controller 40 in accordance with a frame rate that is appropriately calculated by the frame rate calculating unit 59 to execute the DA imaging of the extremity of the patient P.

Note that the frame rate calculating unit 59 may have a correlation table in advance in which blood-vessel data, for example, blood-vessel diameters and frame rates are associated with each other, and may calculate a frame rate with reference to a blood-vessel diameter calculated by the blood-vessel data calculating unit 58 on the correlation table. The frame rate calculating unit 59 may further have a plurality of correlation tables so that, after selecting a desired correlation table, the frame rate calculating unit 59 can calculate a frame rate with reference to a blood-vessel diameter calculated by the blood-vessel data calculating unit 58 on the desired correlation table.

Figure 12:
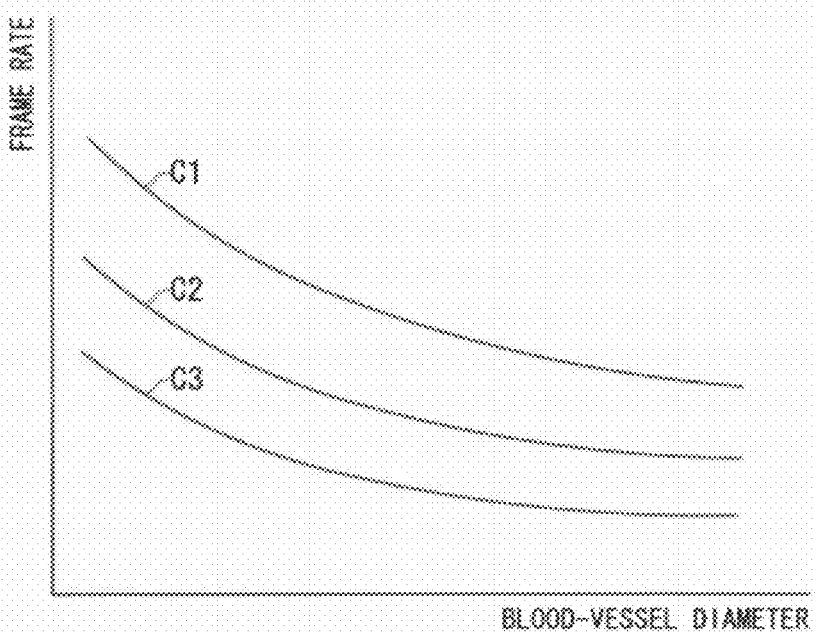
FIG. 12 is a diagram showing an example of plurality of correlation tables in graphical form.

FIG. 12 is a diagram showing an example of the plurality of correlation tables in graphical form.

FIG. 12 shows the relationship between blood-vessel data, for example, blood-vessel diameters, and frame rates with three correlation curves (correlation curves C1, C2, and C3). If the angiography apparatus 10B stores the correlation curves C1, C2, and C3 in advance, the frame rate calculating unit 59 can set the next frame rate on the basis of the correlation curve C selected by the operator and blood-vessel data calculated by the blood-vessel data calculating unit 58.

Figure 13:
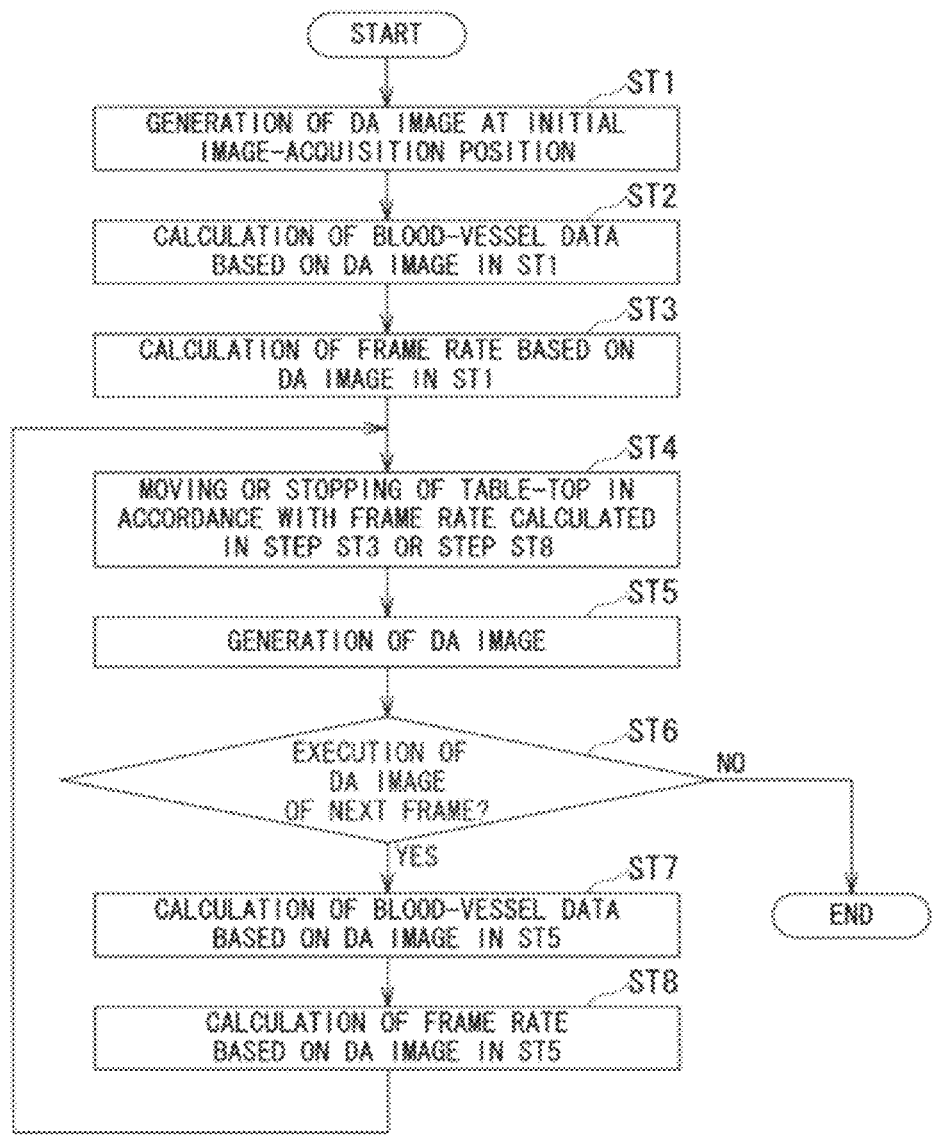
FIG. 13 is a flowchart showing an operation of the X-ray image diagnosing apparatus of the third embodiment.

Next, the operation of the angiography apparatus 10B of the third embodiment will be described with reference to a flowchart shown in FIG. 13.

The angiography apparatus 10B executes DA imaging at an initial image-acquisition position in the entire image-acquisition region to generate a DA image at the initial image-acquisition position (step ST1).

The angiography apparatus 10B extracts blood vessels using the luminance of the DA image generated in step ST1 and calculates at least one of the diameters of the blood vessels and the luminance values of the blood vessels (concentration of a contrast medium) as blood-vessel data (step ST2). In step ST2, for example, the blood-vessel diameters, or the blood-vessel data, are calculated.

The angiography apparatus 10B calculates the next frame rate for DA imaging, with the table-top 25 moved in the longitudinal direction with respect to the C-arm 23, on the basis of the blood-vessel diameters calculated in step ST2 (step ST3).

The angiography apparatus 10B moves the table-top 25 to the next image-acquisition position (stop position) and stops it in accordance with the frame rate calculated in step ST3 or step ST8, to be described later (step ST4). Next, the angiography apparatus 10B executes DA imaging at the image-acquisition position at which the table-top 25 is stopped in step ST4 to generate a DA image at the image-acquisition position (step ST5). The DA image generated in step ST5 is displayed on the fluoroscopic monitor 34*a* substantially in real time.

The angiography apparatus 10B determines whether to execute DA imaging of the next frame in the image-acquisition region (step ST6). If the determination in step ST6 is YES, that is, if the angiography apparatus 10B determines to execute the DA imaging of the next frame in the image-acquisition region, the angiography apparatus 10B extracts blood vessels on the basis of the luminance of the DA image generated in step ST5 and calculates the diameters of the blood vessels as blood-vessel data (step ST7).

The angiography apparatus 10B calculates the next frame rate for DA imaging, with the table-top 25 moved in the longitudinal direction with respect to the C-arm 23, on the basis of the blood-vessel diameters calculated in step ST7 (step ST8).

On the other hand, if the determination in step ST6 is NO, that is, if the angiography apparatus 10B determines not to execute the DA imaging of the next frame in the image-acquisition region, the angiography apparatus 10B concludes the DA imaging.

Although the angiography apparatus 10B is described when applied to stepping the DA imaging of the entire image-acquisition region, the present invention is not limited thereto. For example, the angiography apparatus 10B takes angiograms in accordance with an appropriately calculated frame rate while moving the table-top 25 in the longitudinal direction at a fixed speed. That is, the angiography apparatus 10B may adopt an image-acquisition method of covering the entire image-acquisition region while continuously moving the table-top 25 irrespective of the frame rate. With this image-acquisition method, the DA image acquiring unit 57 controls the system controller 40 in accordance with a calculated frame rate to repeat image-acquisition during the movement of the table-top 25.

With the angiography apparatus 10B according to the third embodiment, the number of image-acquisitions of thick blood vessels can be decreased, X-ray exposure of the patient P can be reduced. Moreover, with the angiography apparatus 10B, the image-acquisition position is automatically determined depending on an appropriately calculated frame rate, so that there is no need for the operator to set the image-acquisition position in advance, which provides the operator with an optimum X-ray image diagnosing environment.

What is claimed is:

1. An X-ray image diagnosing apparatus comprising:
  a radiating unit configured to radiate X-rays;
  a placement unit which is placeable an object;
  a detecting unit configured to detect X-rays that passed through the object;
  a supporting unit configured to support the radiating unit and the detecting unit in opposing relationship across the placement unit;
  a moving control unit configured to relatively move the supporting unit and the object on a longwise direction of the placement unit so as to perform an X-ray imaging at different imaging positions along the longwise direction;
  an obtaining unit configured to obtain X-ray image by performing the X-ray imaging;
  a calculating unit configured to calculate blood-vessel data indicating at least one of diameters and concentrations of blood vessels on the basis of the X-ray image, and to calculate a frame rate on the basis of the blood-vessel data; and a frame rate control unit configured to change the frame rate on the X-ray imaging.

2. The X-ray image diagnosing apparatus according to claim 1, wherein, the calculating unit calculates a relatively low frame rate if the blood-vessel diameter is greater than or equal to a threshold value, and calculates a relatively high frame rate if the blood-vessel diameter is less than the threshold value.

3. The X-ray image diagnosing apparatus according to claim 1, wherein, the calculating unit calculates a relatively low frame rate if the concentration of the blood vessel is greater than or equal to a threshold value, and calculates a relatively high frame rate if the concentration of the blood vessel is less than the threshold value.

4. The X-ray image diagnosing apparatus according to claim 1, further comprising, a storage unit configured to store correlation tables in which the blood-vessel data and the frame rates are associated with each other, wherein, the calculating unit calculates the frame rate with reference to the calculated blood-vessel data on a desired correlation table selected from the correlation tables.

5. The X-ray image diagnosing apparatus according to claim 1, wherein, the X-ray imaging is a digital angiography (DA) imaging.

6. An X-ray image diagnosing apparatus comprising:

a radiating unit configured to radiate X-rays;

a placement unit which is placeable an object;

a detecting unit configured to detect X-rays that passed through the object;

a supporting unit configured to support the radiating unit and the detecting unit in opposing relationship across the placement unit;

a moving control unit configured to relatively move the supporting unit and the object on a longwise direction of the placement unit so as to perform an X-ray imaging at a plurality of imaging positions along the longwise direction;

a first obtaining unit configured to obtain first X-ray images by performing a first X-ray imaging in accordance with a single frame rate;

a calculating unit configured to calculate blood-vessel data indicating at least one of diameters and concentrations of blood vessels on the basis of the first X-ray images;

a setting unit configured to preliminarily set, on the basis of the blood-vessel data, an imaging condition so that different frame rates are associated with the respective imaging positions; and a second obtaining unit configured to obtain second X-ray images by performing the X-ray imaging on the frame rates corresponding to the respective imaging positions in accordance with the imaging condition.

7. The X-ray image diagnosing apparatus according to claim 6, wherein, the second obtaining unit uses a relatively low frame rate for an imaging position of the imaging positions at which the blood-vessel diameters are greater than or equal to a threshold value, and uses a relatively high frame rate for an imaging position at which the blood-vessel diameters are less than the threshold value.

8. The X-ray image diagnosing apparatus according to claim 6, further comprising, a generating unit configured to generate a long image by overlapping parts of the second X-ray images, wherein, the generating unit overlaps the parts of the X-ray images in accordance with the information of the imaging positions individually added to the second X-ray images.

9. The X-ray image diagnosing apparatus according to claim 6, further comprising, a generating unit configured to generate a long image by overlapping parts of the second X-ray images, wherein, the generating unit extracts the edges of the blood vessels on the basis of differences in luminance values on the second X-ray images, and overlaps the parts of the second X-ray images so as to connect the blood vessels.

10. The X-ray image diagnosing apparatus according to claim 6, further comprising, a generating unit configured to generate a long image by overlapping parts of the second X-ray images, wherein, the generating unit sets a luminance value of the parts at which the second X-ray images overlap as an average value of luminance values corresponding to the parts.

11. The X-ray image diagnosing apparatus according to claim 10, wherein, the generating unit performs filtering by comparing the average value and a weighted noise detection threshold.

12. The X-ray image diagnosing apparatus according to claim 6, further comprising, a generating unit configured to generate a long image by overlapping parts of the second X-ray images, wherein, the generating unit sets a luminance value of the parts at which the second X-ray images overlap as the most numerous value of luminance values corresponding to the parts.

13. The X-ray image diagnosing apparatus according to claim 6, wherein, the first and second X-ray imagings are a digital subtraction angiography (DSA) imaging.

14. A controlling method of an X-ray image diagnosing apparatus including a radiating unit configured to radiate X-rays, a placement unit which is placeable an object, a detecting unit configured to detect X-rays that passed through the object, and a supporting unit configured to support the radiating unit and the detecting unit in opposing relationship across the placement unit, comprising;

a moving control step of relatively moving the supporting unit and the object on a longwise direction of the placement unit so as to perform an X-ray imaging at different imaging positions along the longwise direction;

an obtaining step of obtaining X-ray image by performing the X-ray imaging;

a calculating step of calculating blood-vessel data indicating at least one of diameters and concentrations of blood vessels on the basis of the X-ray image, and calculating a frame rate on the basis of the blood-vessel data; and a frame rate control step of changing the frame rate on the X-ray imaging.

15. The controlling method according to claim 14, wherein, the calculating step calculates a relatively low frame rate if the blood-vessel diameter is greater than or equal to a threshold value, and calculates a relatively high frame rate if the blood-vessel diameter is less than the threshold value.

16. The controlling method according to claim 14, wherein, the calculating step calculates a relatively low frame rate if the concentration of the blood vessel is greater than or equal to a threshold value, and calculates a relatively high frame rate if the concentration of the blood vessel is less than the threshold value.

17. The controlling method according to claim 14, further comprising,
 a storage step of storing correlation tables in which the blood-vessel data and the frame rates are associated with each other, wherein,
 the calculating step of calculating the frame rate with reference to the calculated blood-vessel data on a desired correlation table selected from the correlation tables.

18. The controlling method according to claim 14, wherein,
 the X-ray imaging is a digital angiography (DA) imaging.

19. A controlling method of an X-ray image diagnosing apparatus including a radiating unit configured to radiate X-rays, a placement unit which is placeable an object, a detecting unit configured to detect X-rays that passed through the object, and a supporting unit configured to support the radiating unit and the detecting unit in opposing relationship across the placement unit, comprising:
 a moving control step of relatively moving the supporting unit and the object on a longwise direction of the placement unit so as to perform an X-ray imaging at a plurality of imaging positions along the longwise direction;
 a first obtaining step of obtaining first X-ray images by performing a first X-ray imaging in accordance with a single frame rate;
 a calculating step of calculating blood-vessel data indicating at least one of diameters and concentrations of blood vessels on the basis of the first X-ray images;
 a setting step of preliminarily setting, on the basis of the blood-vessel data, an imaging condition so that different frame rates are associated with respective imaging positions; and
 a second obtaining step of obtaining second X-ray images by performing the X-ray imaging on the frame rates corresponding to the respective imaging positions in accordance with the imaging condition.

20. The controlling method according to claim 19, wherein,
 the second obtaining step of using a relatively low frame rate for an imaging position of the imaging positions at which the blood-vessel diameters are greater than or equal to a threshold value, and using a relatively high frame rate for an imaging position at which the blood-vessel diameters are less than the threshold value.

* * * * *